(12) United States Patent
Hanson

(10) Patent No.: US 6,279,782 B1
(45) Date of Patent: Aug. 28, 2001

(54) DENTAL RINSE BOTTLE WITH QUICK CONNECT

(75) Inventor: Richard W. Hanson, Beaverton, OR (US)

(73) Assignee: Dental Components, Inc., Newberg, OR (US)

( * ) Notice: Subject to any disclaimer, the term of this patent is extended or adjusted under 35 U.S.C. 154(b) by 25 days.

(21) Appl. No.: 09/687,761
(22) Filed: Oct. 13, 2000
(51) Int. Cl.[7] .................................................. B65D 83/14
(52) U.S. Cl. ................................... 222/153.09; 222/400.7
(58) Field of Search ................................... 222/397, 325, 222/153.11, 153.09, 400.7

(56) References Cited

U.S. PATENT DOCUMENTS

Re. 29,405 * 9/1977 Gunzel, Jr. et al. .................. 222/335
5,836,483 * 11/1998 Disel ................................. 222/400.7

* cited by examiner

Primary Examiner—Philippe Derakshani
(74) Attorney, Agent, or Firm—James D. Givnan, Jr.

(57) ABSTRACT

A bottle for a dental rinse has a neck component provided with vertical and inclined channels to receive bayonet lock arms on a cap to lock the neck component to the cap. The bayonet arms project from a cap stem which is provided with an O-ring. Annular wall surfaces on the neck component alternately cooperate with the O-ring to seal and to vent the bottle during axial positioning of the neck component. The cap is mounted on a support and includes pressure and liquid carrying passageways in communication with the bottle.

9 Claims, 4 Drawing Sheets

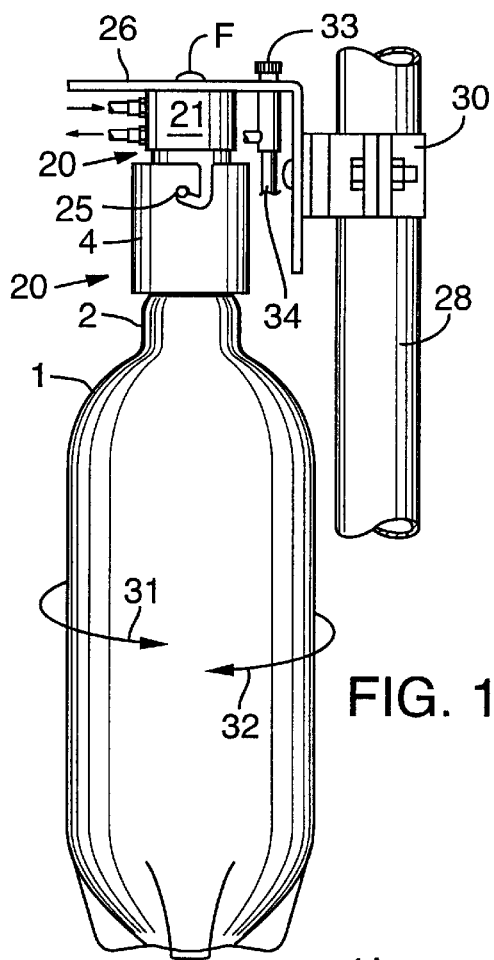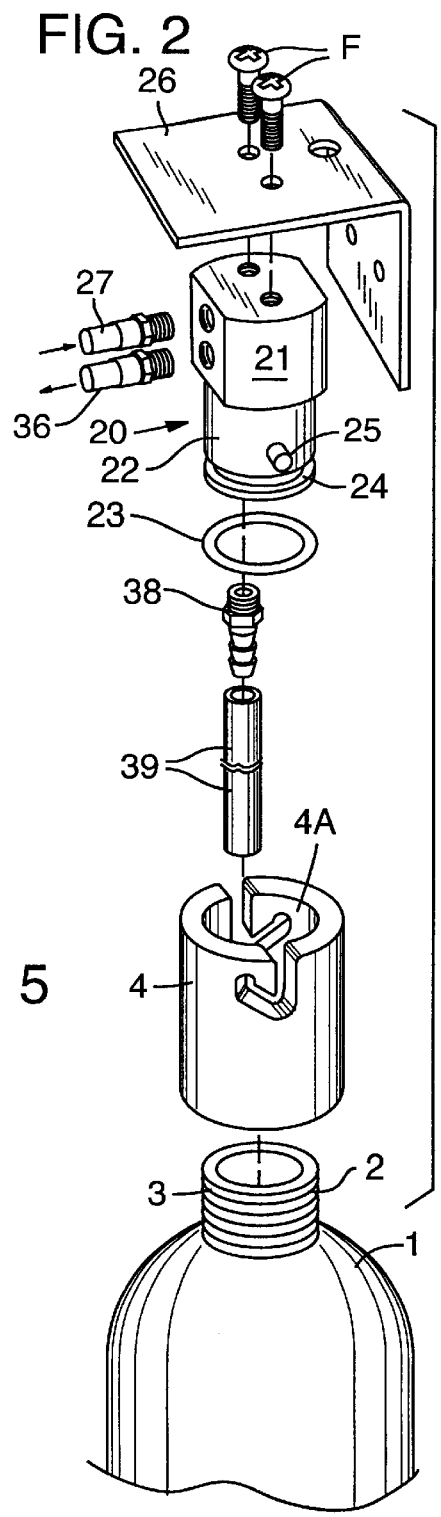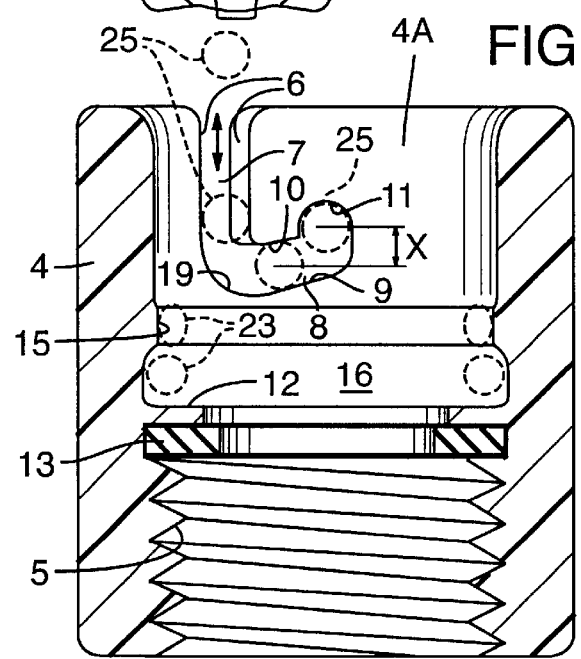
FIG. 1
FIG. 2
FIG. 5

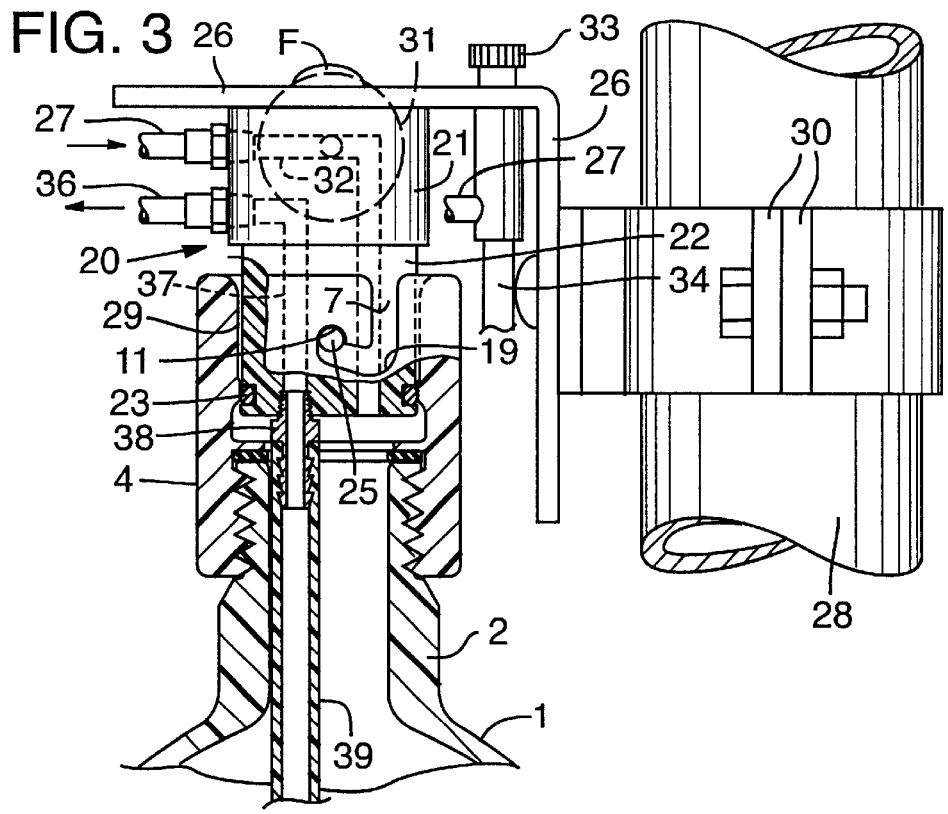
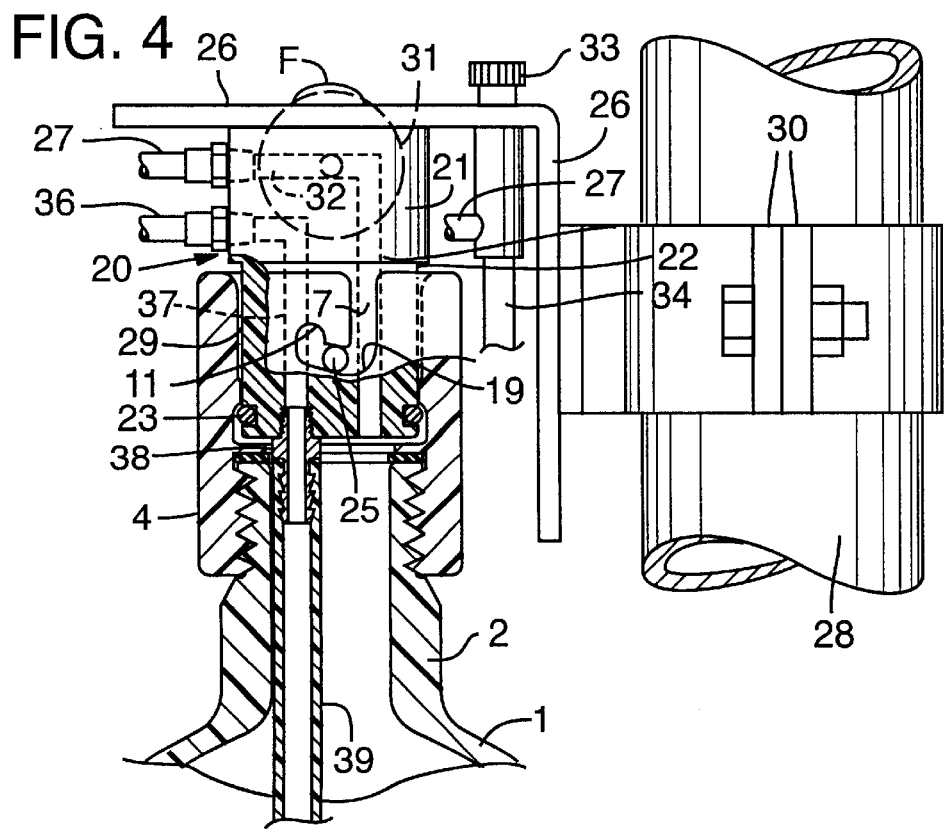

DENTAL RINSE BOTTLE WITH QUICK CONNECT

BACKGROUND OF THE INVENTION

The present invention pertains generally to pressurized containers and the bleeding of pressure prior to container opening.

In the field of dentistry, it is accepted practice to rinse the patient's mouth at intervals. While tap water is used for such rinsing, it is preferable to use distilled water or a rinse made specifically for such a purpose. In such a case, the rinse liquid is contained in a bottle or other container adjacent the dental chair and supplied with modest air pressure to provide a pressurized flow to the dental syringe. Such a practice of providing a rinse from a pressurized bottle or other container incurs the task of frequently having to refill the bottle with liquid, which requires the pressure being bled prior to opening. To do so without careful venting can result in a somewhat dynamic separation of the container from its closure. Should a supply of rinse be exhausted during patient treatment the assistant, in haste to refill the bottle, may fail to open the rinse container or bottle in a slow, controlled manner, resulting in some risk. The use of a bleed valve requires an additional task of the assistant, and is not practical in that they may be overlooked in a busy environment.

SUMMARY OF THE PRESENT INVENTION

The present invention concerns the provision of a pressurized liquid container with a quick connect system which automatically bleeds off pressure during opening of the container.

In a dental office, a container for a rinse liquid may be located adjacent a dental chair or station and is in communication with a hand held three-way syringe and dental handpieces operated by the dentist or assistant. The rinse quantity may not be checked, in view of the container being somewhat out of the field of vision.

The present system includes a cap having a seal which seats against an annular wall located within a neck component of the container. The neck component and cap share a modified bayonet type lock. Axial movement occurring between the cap and neck component during locking and unlocking of the neck component automatically seals and unseals the cap to neck component.

Important objectives of this system include the provision of a pressurized container that automatically bleeds off pressure during unlocking a container and prior to separation of the container from its cap or closure; the provision of a pressurized container utilizing a bayonet type lock to secure the container to its cap and having inclined channels which act on bayonet type locking pins to impart relative axial movement between cap and the container neck to unseat a seal, permitting safe bleeding off of container pressure prior to bayonet lock separation; the provision of a cap type closure for a pressurized container or bottle with a stem having bayonet lock type pins or arms which ride in channels in a neck of the container, inclined to the container major axis, to impart axial displacement of a seal away from sealing engagement with the neck to vent the container; the provision of a pressurized container for a dental rinse liquid having a closure and neck portion which automatically bleed container pressure prior to separation to avoid dynamic separation and risk of injury.

BRIEF DESCRIPTION OF THE DRAWINGS

In the accompanying drawings:

FIG. 1 is an elevational view of a rinse bottle coupled to a pole support;

FIG. 2 is an exploded view of the rinse bottle with neck component and cap with a bracket for pole attachment;

FIG. 3 is a sectional view of the neck component on the bottle in sealed engagement with a cap;

FIG. 4 is a view similar to FIG. 3 but with the neck component partially unlocked from the cap for pressure bleeding;

FIG. 5 is a vertical sectional view of the neck component with an O-ring shown in broken lines and with a bayonet lock arm shown in multiple positions during unlocking of the neck component.

DETAILED DESCRIPTION OF THE PREFERRED EMBODIMENTS

Figure 6:
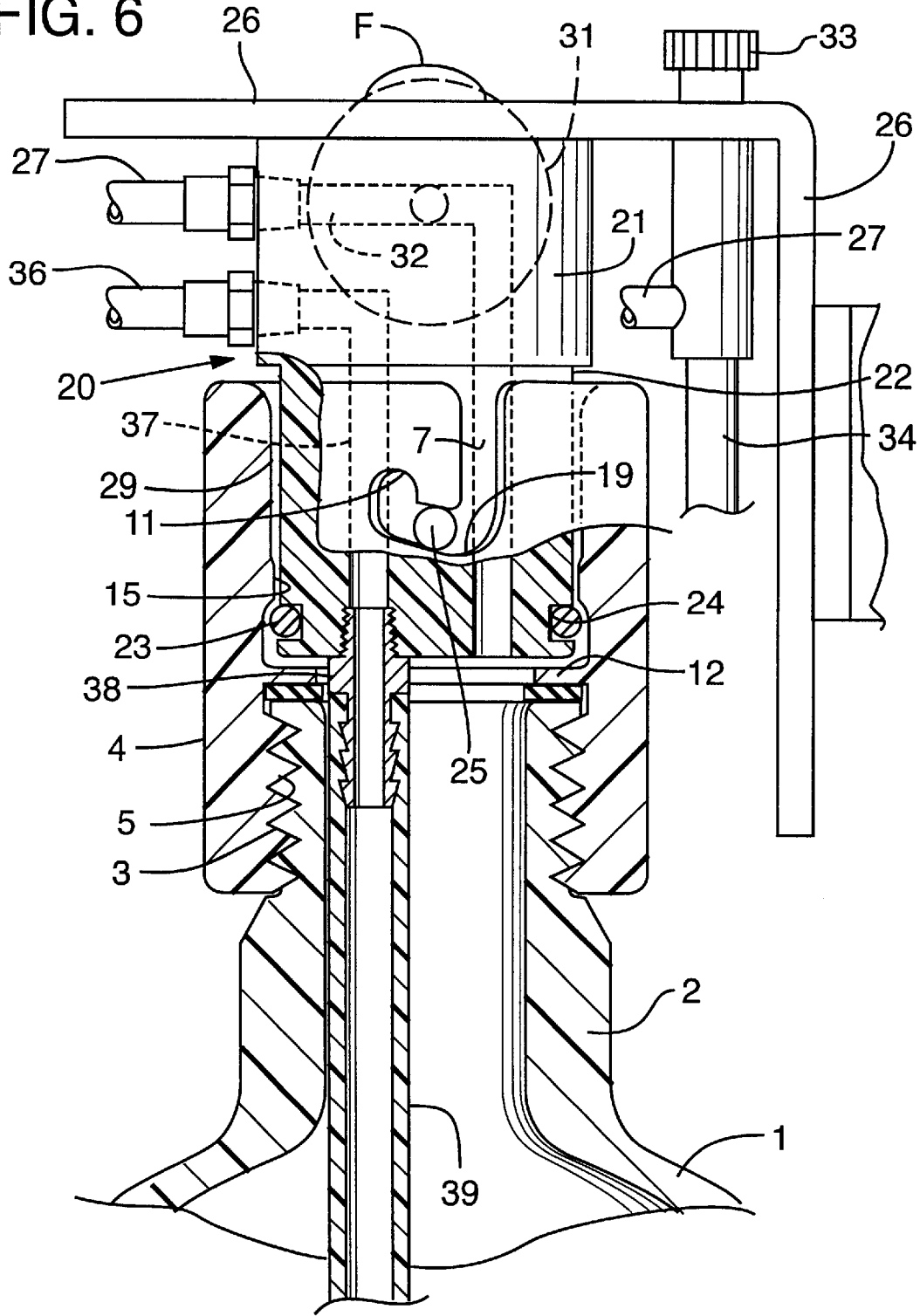
FIG. 6 is an enlarged sectional view of the neck component and cap in a pressure bleeding relationship.

With continuing attention to the drawings wherein applied reference numerals indicate parts similarly hereinafter identified, the reference numeral 1 indicates a bottle of heavy duty construction terminating upwardly in a neck 2 having male threads 3 thereon.

A neck component 4 includes internal threads 5 for engagement with bottle threads 3. Neck component 4 has a central open area 4A. Vertical edges 6 on component 4 define a vertical channel 7 which is part of a bayonet type lock with the vertical channels each merging with an inclined channel 8 defined by inclined edges 9 and 10 of the neck component. An internal flange 12 retains a washer 13 in place.

A cap is indicated generally at 20 and includes a head 21 and a stem 22 the latter provided for insertion into opening 4A of neck component 4. An O-ring seal at 23 is carried within a stem groove 24. Bayonet lock arms as at 25 project radially from the cap. Bayonet lock arms 25, during coupling of the neck component to the cap, pass through vertical channels 7 of the neck component and thence into inclined channels 8 and ultimately, in a locked condition, seat within detents 11. A transition edge 19 ensures imparting rotation to component 4 to locate an edge 10 over an arm 25.

In a preferred embodiment, cap 20 is secured to a support having a bracket 26 and fasteners F with the bracket being coupled to a post 28 by means of a clamp 30. Cap 20 is thus held fixed in place while vertical movement of the neck component 4 occurs during manual rotation of bottle 1 during installation and subsequent detachment of bottle 1. It will be seen that vertical channels 7 receive bayonet arms 25 with the arms ultimately passing through inclined channels 8 during counterclockwise bottle and neck component rotation indicated by arrow 31.

During attachment of the neck component to cap 20, O-ring 23 will seat against first annular wall 15, upon bayonet locking arms seating in detents 11, to seal bottle 1. Conversely, opposite rotation per arrow 32 to bottle 1 requires upward movement of the bottle to release arms 25 from detents 11, and then to cause neck component 4 and bottle 1 to be displaced further upwardly as the uppermost inclined channel edge 10 rides past bayonet locking arm 25. The vertical component x of neck component travel is of a magnitude to cause neck component 4 to be displaced upwardly to the extent O-ring seal 23 is now relocated in a vent space partially defined by second annular wall 16, of greater diameter than wall 15, to permit escape of pressure past O-ring 23 and upwardly through wall clearance 29 between the neck component and stem 22 therein to bleed off bottle pressure all prior to bayonet arms 25 entering vertical channels 7.

Cap 20 is preferably provided with a pressure gauge 31 responsive to pressure in a cap passageway 32 controlled by a pressure regulator 33. A pressure source is at 34 is typically available on most all dental units. Source 34 is controlled by an ON-OFF toggle valve (not shown) preferable located on bracket 26 with a pressure line 27 serving cap passageway 32. A liquid discharge passageway at 37 is provided with a barb 38 which receives the outer end of a discharge tube 39. A flexible conduit 36 serves a dental syringe or a dental handpiece.

In use, upon interruption of air pressure to bottle 1 by the closure of the ON-OFF toggle switch, earlier noted, bottle 1 (still pressurized) is manually rotated per arrow 32 to cause stationary bayonet lock arms 25 to impart a lifting force to inclined channel edge 10 of neck component 4 to lift same and importantly lift second annular wall 16 into place about O-ring 23 whereat pressure in the bottle is bled off through the vent space defined by wall 16 and the outer peripheral surface of the O-ring.

Figure 7:
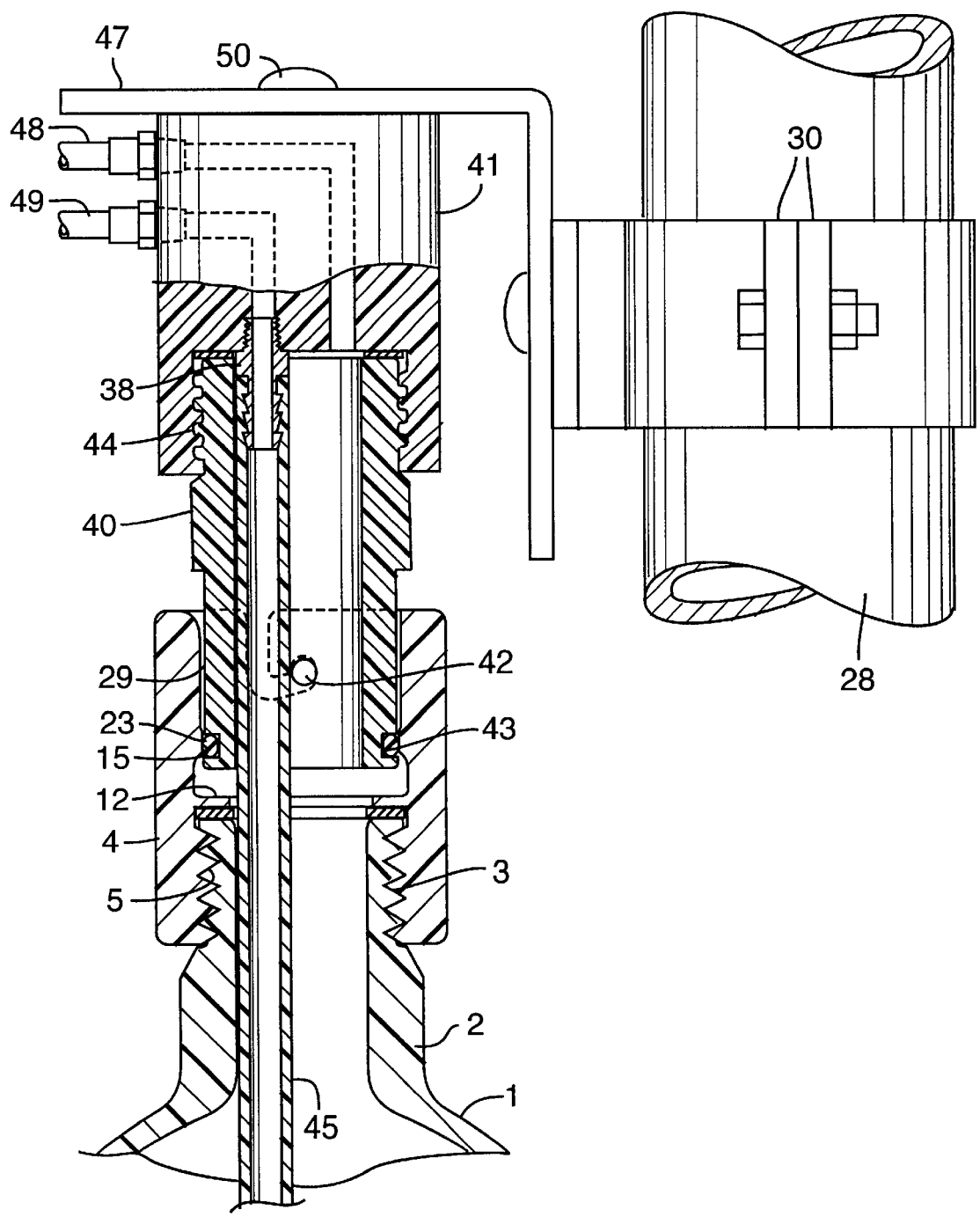
FIG. 7 is a sectional view of the neck component and modified cap.

In FIG. 7 a modified cap is indicated at 40 for use in retrofitting a rinse bottle cap at 41 carried by a support 47. The modified cap 40 is tubular with bayonet locking arms as at 42 and an O-ring receiving groove 43. The rinse bottle cap 41 is internally threaded to receive threads 44 of cap 40. A discharge tube 45 depends from earlier cap 41 which cap is also served by line 48 and a discharge conduit 49 and is provided with female threads to receive bracket attaching screws 50.

While I have shown but a few embodiments of the invention, it will be apparent to those skilled in the art that the invention may be embodied still otherwise without departing from the spirit and scope of the claimed invention.

Having thus described the invention, what is desired to be secured by a Letters Patent is:

1. In combination with a container for receiving a liquid subjected to a gas at above atmospheric pressure, the improvement comprising, a cap having a stem, a seal on said stem, a neck component on the container having a first annular wall engageable with said seal to close the container, a second annular wall axially spaced from and of greater diameter than said first annular wall and partially defining a vent passageway, and a lock including arms, channels for reception of said arms including vertical channels defined by upright edges and inclined channels defined by inclined edges inclined to the axis of the neck component with relative movement between said arms and the inclined edges imparting axial movement to said neck component and the seal thereon alternately toward and away from said first and said second annular walls to seal and to vent the container with the latter occurring prior to separation of the cap and the neck component.

2. The improvement claimed in claim 1 wherein said cap defines an inlet pressure passageway and a liquid outlet passageway.

3. The improvement claimed in claim 1 wherein said seal is an O-ring.

4. The improvement claimed in claim 1 wherein said inclined channels each have an end segment including a detent occupied by an arm when the cap and neck component are locked together.

5. The improvement claimed in claim 1 additionally including a support, said cap affixed to said support.

6. The improvement claimed in claim 1 wherein the vertical component of bayonet arm travel along said inclined channels is greater than the vertical travel of said seal to disengage said first annular wall to affect opening of the vent passageway prior to entry of the bayonet arms into those channels defined by said upright edges to ensure venting of the container prior to unlocking of the cap and neck component.

7. A cap assembly for a pressurized bottle permitting automatic venting of the bottle during opening of same, said cap assembly including, a support, a cap on said support served by a pressure inlet line and a liquid outlet conduit, a stem having an O-ring and bayonet lock arms, and a neck component of the bottle including a first annular wall for sealing engagement with said O-ring, a second annular wall of greater diameter than said first annular wall and axially offset from said first annular wall, a second bayonet locking member including vertical edges and inclined edges defining arm receiving channels with the inclined edges inclined to the major axis of the neck component locking engagement with said bayonet lock arms, said bayonet lock arms engageable with said inclined edges upon manual rotation of the neck component imparting axial travel to the neck component and bottle to position said first annular wall into sealing engagement with said O-ring and oppositely upon partial rotation of the neck component in the opposite direction positioning said second annular wall radially offset from said O-ring to vent bottle pressure through a vent space about said O-ring.

8. The cap assembly claimed in claim 7 wherein said cap additionally includes external threads for threaded engagement of the cap with a cap having internal threads in place on said support for retrofitting purposes.

9. The combination claimed in claim 1 wherein the vertical channels and the inclined channels are joined by transition curved edges with each of said curved edges terminating subjacent one of said inclined edges to prevent neck component separation by gravity.

* * * * *